United States Patent [19]

McMahon

[11] Patent Number: 5,332,087
[45] Date of Patent: Jul. 26, 1994

[54] PROTECTIVE DEVICE FOR CONDOMS

[76] Inventor: Phillip J. McMahon, 1767 Monterey Dr., Apt. 106, Palm Bay, Fla. 32905

[21] Appl. No.: 967,833

[22] Filed: Oct. 28, 1992

Related U.S. Application Data

[63] Continuation-in-part of Ser. No. 888,853, May 27, 1992, abandoned.

[51] Int. Cl.⁵ .................. B65D 85/14; A45C 1/06; A45C 11/00
[52] U.S. Cl. .................. 206/69; 150/132
[58] Field of Search .................. 206/0.8-0.84, 206/39.4, 39.5, 69; 150/131, 132, 136, 145, 150

[56] References Cited

U.S. PATENT DOCUMENTS

| | | | |
|---|---|---|---|
| 1,116,660 | 11/1914 | Willis | 206/0.81 X |
| 1,509,861 | 9/1924 | Coleman | 206/0.81 |
| 2,006,212 | 6/1935 | Grabler | 206/69 |
| 2,008,875 | 7/1935 | Peterson et al. | 206/69 |
| 2,185,359 | 1/1940 | Swanson | 206/0.81 |
| 2,321,254 | 6/1943 | Schmid | 206/69 |
| 2,390,748 | 12/1945 | Swanson | 206/0.81 X |
| 2,569,629 | 10/1951 | Everitt | 206/0.81 X |
| 2,616,554 | 11/1952 | Wade et al. | 206/0.84 |
| 2,671,384 | 3/1954 | D'Ambrosio | 150/131 X |
| 3,062,364 | 11/1962 | Ziemski | 206/0.84 X |
| 3,080,963 | 3/1963 | Rothgart | 206/0.84 |
| 3,316,924 | 5/1967 | Ware | 206/0.84 X |
| 3,882,916 | 5/1975 | Margolis | 150/132 |
| 4,450,955 | 5/1984 | Featherston | 206/39.6 |
| 4,741,372 | 5/1988 | Santilli | 206/39 X |
| 4,741,434 | 5/9188 | Liebman | 206/69 X |
| 4,776,460 | 10/1988 | Hoffman | 206/69 |
| 4,805,820 | 2/1989 | Kearney et al. | 206/37 X |
| 4,892,188 | 1/1990 | Meadows | 206/69 X |
| 5,117,841 | 6/1992 | McBeth | 206/69 X |
| 5,172,430 | 12/1992 | Lerma-Solis | 206/69 X |

FOREIGN PATENT DOCUMENTS

| | | | |
|---|---|---|---|
| 2519924 | 11/1976 | Fed. Rep. of Germany | 206/0.8 |
| 2644436 | 9/1990 | France | 206/69 |
| 25452 | of 1912 | United Kingdom | 150/150 |

*Primary Examiner*—Sue A. Weaver
*Attorney, Agent, or Firm*—Camoriano & Smith

[57] ABSTRACT

A combination of a condom package and receptacle for holding a condom package comprising an essentially square condom package having a condom centrally disposed therein and forming a central body portion of a predetermined thickness tapering to a flat perimeter region circumscribing the central body portion. The receptacle is adapted to receive and hold the condom package and comprises a planar first surface and a second surface which is essentially rectangular in plan. The second surface is connected to the first surface along three edges thereof with the surfaces collectively defining a mouth for receiving the condom package and along the connecting junctures between the surfaces forming a pair of guides. The guide surfaces serve to guide the opposing perimeter edges of the condom package upon insertion. The second surface defines a concavity with respect to the planar surface approximating the configuration of one side of the condom package and forming a taper angle with the first surface about equal to the taper angle of the condom package.

4 Claims, 2 Drawing Sheets

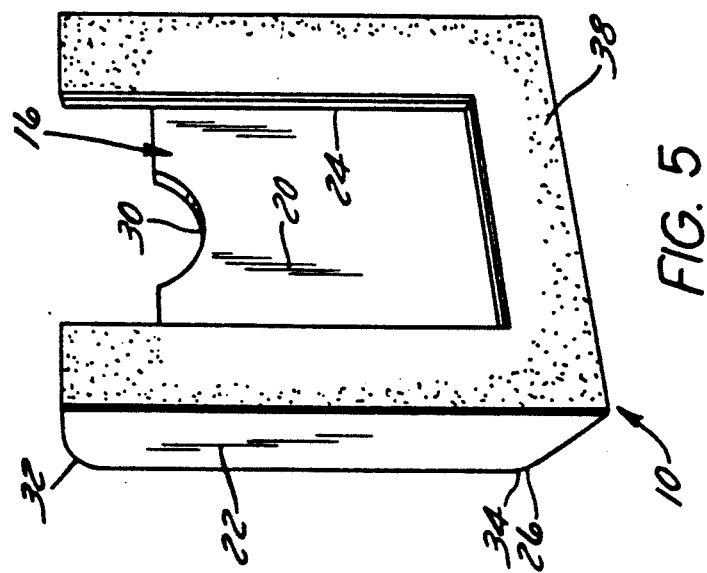
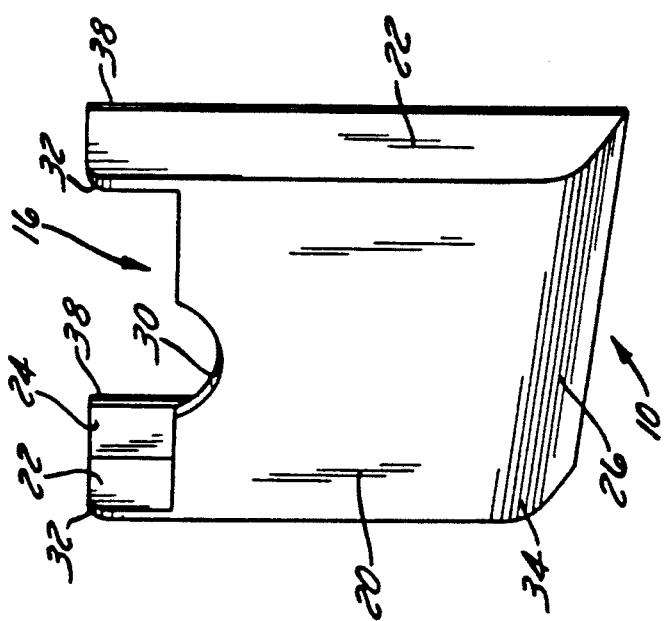
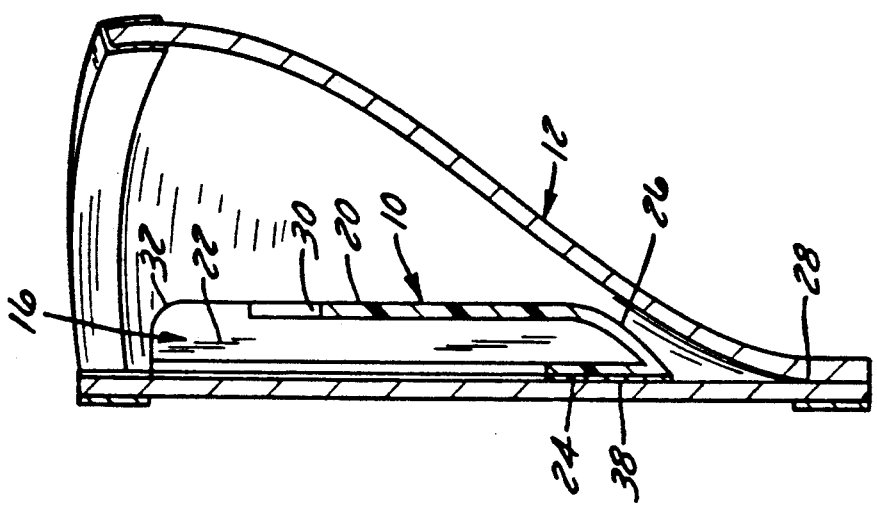

PROTECTIVE DEVICE FOR CONDOMS

RELATED INVENTIONS

This application is a continuation-in-part of U.S. application Ser. No. 07/888,853 filed on May 27, 1992, abandoned.

FIELD OF THE INVENTION

The present invention relates generally to a small receptacle for carrying items in a wallet and the like and, more particularly, to a receptacle for carrying fragile objects such as a condom package.

BACKGROUND OF THE INVENTION

Wallets lack clearly defined spaces for the placement and protection of prophylactic packages such as condoms. Condoms are receiving increasing acceptance by the populace to preclude contraception and prevent the further spread of communicable sexually transmitted diseases such as AIDS. A typical practice for the carrying of condom packages is the placement thereof in a billfold hidden for easy access when needed. However, normal daily activities causes a billfold to chafe the condom packages and to crack or peel them. As a consequence, the package seals are frequently broken, thereby destroying product freshness and conceivably the condom. Therefore, the need exists for a device capable of stowing condoms in wallets free of damage.

In the past, protective holders for carrying personal items have been developed. For instance, U.S. Pat. No. 1,466,729, issued Sep. 4, 1923 to Ray P. Riley, discloses a holder for keeping tickets, labels or the like in a clean and fresh condition. The holder consists of two parts, a body part and a back part which slides into grooves of the body part exerting pressure on the contents of the holder. Additionally, U.S. Pat. No. 4,450,955, issued May 29, 1984 to Elmer F. Featherston, discloses a protective holder for information bearing cards carried in pockets or purses. The holder is fabricated from a primary wall portion having opposite lateral edges folded over and superimposed over the primary portion and spaced therefrom. Also, U.S. Pat. No. 3,244,211, issued Apr. 5, 1966 to James L. Byers et al, shows a card holder adapted for insertion into a wallet or billfold. A sheath open at both ends envelopes ejecting slides and has an open bottom or back wall and a closed top or front wall. Further, U.S. Pat. No. 4,741,372, issued May 3, 1988 to Michael A. Santilli, discloses flexible envelopes for a pocket organizer. The envelopes insert into pockets of the organizer and are open at their top ends. No means are provide to prevent chafing of a prophylactic package carried therein. Finally, U.S. Pat. No. 4,805,820, issued Feb. 21, 1989 to Thomas G. Kearney, discloses a portable receptacle for prophylactic packages. A cut-out portion is formed with grooves to accommodate a single condom package. A pivotable lid closes the holder and must be again opened to remove contents of the receptacle. The receptacle is not adapted for use in wallets.

None of the above inventions and patents, taken either singly or in combination to describe the instant protective holder as claimed.

SUMMARY OF THE INVENTION

By the present invention, an easily accessible carrying case is disclosed which provides for protective storage and retention of condoms in billfolds. Accordingly, it is a principal object of the invention to provide a storage receptacle for use in wallets and the like for the carrying and retention of condom packages.

It is another object of the invention to provide a condom storage and retention receptacle for wallets that may be readily installed in pocket wallets of various sizes.

It is a further object of the invention to provide a carrying case that maintains condom packages easily accessible while protecting the contents thereof from damage and in a sanitary condition.

Still another object of the invention is to provide a protective condom storage receptacle wherein condom packages are conveniently inserted and removed.

It is a still further object of the invention to provide improved elements and arrangements thereof in a device for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

FIG. 3 is a sectional view along lines 3—3 of FIG. 1.

FIG. 4 is a frontal view of the inventive receptacle illustrated in FIG. 1 and removed from the billfold.

FIG. 5 is a rear view of the inventive receptacle shown in FIG. 4.

Similar reference characters denote corresponding features consistently throughout the attached drawings.

DETAILED DESCRIPTION OF THE PREFERRED EMBODIMENT

Figure 1:
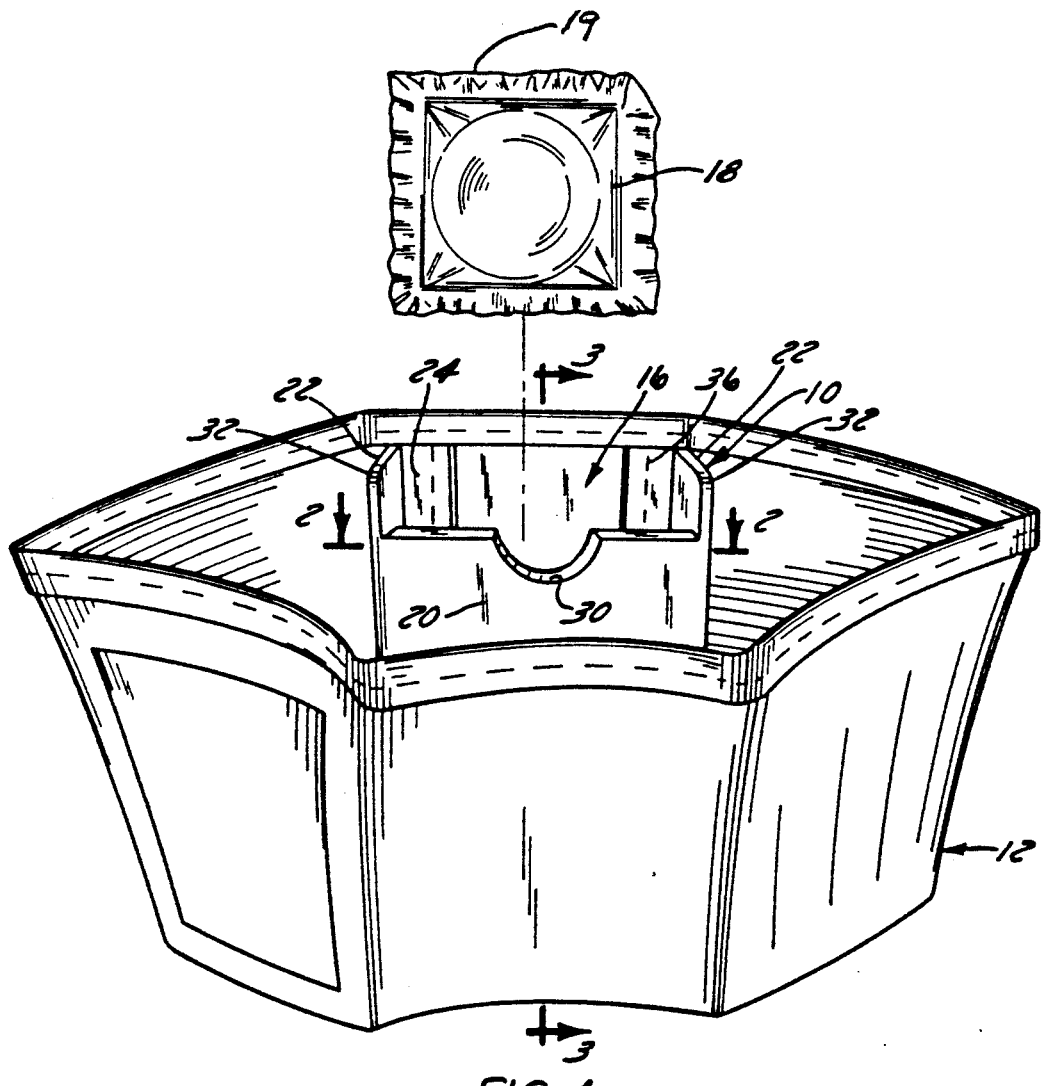
FIG. 1 is a perspective view of a receptacle in accordance with the present invention installed within a conventional billfold.

Referring to the drawings in greater detail, FIG. 1 illustrates holder 10 installed in a conventional billfold 12. Holder 10 has an open end 16 permitting condom package 18 to be stowed therein and carried within billfold 12, free from damage. Packages in holder 10 are partially visible for identification. Holder 10 adds little bulk to the billfold and may be readily utilized without requiring unusual handling or dexterity.

Holder 10 has a front wall 20, a pair of side walls 22, a back wall 24, and a bottom wall 26 as shown generally in FIGS. 1, 3-5. Collectively, the walls define an open end 16 communicating with a storage compartment adapted to receive a condom package 18 containing a condom.

An important aspect of the present invention is to provide a holder having an internal contour that not only permits a condom package 18 to be gently inserted into holder 10 and thereafter to be retained with the holder by the gentle pressure exerted against the package by the inside surfaces of walls 20, 22, 24 and 26. The pressure and frictional forces should be sufficient to resist unintentional separation of the package and holder due to jolting caused by carrying and use of the wallet and the like. On the other hand, it is essential that forces retaining the condom package within the holder are not of such a magnitude that the intentional freeing of the package from the holder does not result in damage to the package itself.

Figure 2:
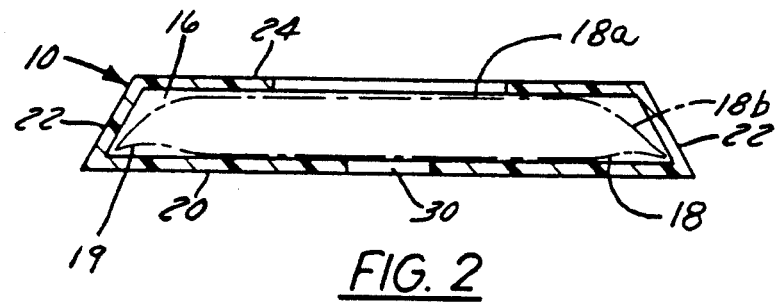
FIG. 2 is an enlarged sectional view taken along lines 2—2 of FIG. 1 with dashed lines to indicate the location of a condom package within the receptacle.

The general shape of a typical one unit condom package is symmetrical, resembling a flat oval with thin edges. The dashed lines in FIG. 2 represent the outline of such a shape. The condom itself is centrally disposed within package 18 and the sides of the package taper toward the perimeter, culminating in the thin tearable edges. Package 18 with the centrally disposed condom has an essentially flat central body portion 18a formed by the spaced and flat opposite sides of the package. Circumscribing central body portion 18a are tapering sides 18b that taper to an essentially flat region 19 (best seen in FIG. 1) bordered by the four tearable edges of the square package 18. The flat region 19 forms an angle A with tapering sides 18b. To provide holder 10 with an internal contour that partially compliments and secures condom package 18 when positioned within holder 10, side walls 22 converge from front wall 20 to back wall 24 and bottom wall 26 is downwardly inclined from front wall 20 to back wall 24. In effect, side walls 22, back wall 24 and bottom wall 26 collectively form a surface with a concavity with respect to front surface 20 as is clearly apparent from a review of FIGS. 2, 3 and 4. The distance between front wall 20 and back wall 24 is preferably about the same thickness of package 18 while the width of the front wall 20 is about the same as the width of a condom package 18. The drawing is not to scale so as to provide a more clear portrayal of the condom package when in place. However, the angle of convergence of side walls 22 preferable approximates the actual taper angle of the condom package.

As condom package 18 is pressed into place, the tapered edges thereof slip into and are guided by the tapers formed by the various walls towards the juncture between walls 22 and wall 20. As condom package 18 is pressed further into holder 10, thus the condom package tends to bow at the center and edges as shown in FIG. 2. Thus, one of the surfaces of condom package 18 becomes increasingly pressed against front wall 22 and the condom package becomes flexed or bowed slightly, particularly at the edges. The edges of package 18 also contact side walls 22 at the boundary with back wall 24. Thus, the pressure and contact of package 18 against the back and side walls provide a securing force sufficient to withstand the normal handling of a billfold and prevent the condom package from becoming loose and damaged.

Bottom wall 26 is inclined as best seen in FIGS. 3 and 4 to facilitate insertion of holder 10 in billfold 12. To insert holder 10, bottom wall 26 is directed toward seam 28 of billfold 12, and holder 10 is slipped into place. Walls of billfold 12 do not have to be widely expanded for the maneuver. Inclined bottom wall 26 can snugly fit between the walls of billfold 12 to give a tight fit near or at seam 28 of billfold 12.

As seen in FIG. 4, side walls 22 have a height greater than primary front wall 20 and are about equal to the height of the condom package 18. Side walls 22 project past front wall 20 for stability. The front wall continues to provide protection to the condom but permits visible inspection. Front wall 20 is cut back to about the upper perimeter of the condom when in position within holder 10. Front upper and lower corners 32, 34 of side walls 22 are rounded to prevent snagging. Open end 16 permits easy access to holder 10 without requiring removal of the contents of billfold 12. At open end 16, front wall 20 has a finger notch or recess 30 therein. Finger recess 30 can aid in grasping the condom for removal or insertion into holder 10 which billfold 12 is open.

Back wall 24 has a large cutout formed therein as seen in FIGS. 1 and 5. The cutout extends from open end 16 toward closed bottom wall 26, thereby reducing back wall 24 to three narrow strips shown in FIG. 5. The large cutout and open end 16 allow easy intentional removal of condom package 18. While cutout is shown as a generally rectangular shape, other configurations such as circular or triangular are also possible.

To secure holder 10 in billfold 12, back wall 24 can De covered with an adhesive material 38 (FIG. 5), or provided with stitching 36 as seen in FIG. 1 for holder 10 to be secured to billfold 12. Although adhesive 38 is shown in FIG. 5, it is contemplated that other fastening means well known in the art may be utilized, such a VELCRO or the like.

Holder 10 may be made from any tough flexible material, such as polypropylene. Durable holder 10 is designed to withstand daily pressures exerted on a conventional billfold carried in articles of clothing or purses. Packages in holder 10 are protected from becoming bent, dirty, scratched, torn and otherwise damaged from abrasion due to contact with billfold 12. While holder 10 is particularly useful for carrying individual prophylactic packages, it will be understood that the invention could be used with a plurality of such packages also.

It is to be understood that the present protective holder is not limited to the sole embodiment described above, but encompasses any and all embodiments within the scope of the following claims.

What is claimed:

1. A portable receptacle usable in a bill fold in combination with a flexible condom package housing a condom, said condom package having a flat central body portion of predetermined thickness with the sides thereof tapering at an angle to a perimeter having edges with a thickness less than said predetermined thickness, and said portable receptacle comprising (a) a first planar surface having a width above the same as the width of said condom package;

(b) a second surface;

(c) a plurality of side wall portions joined to said first surface and converging from said first surface to said second surface at an angle approximately equal to said taper angle of said condom package thereby forming a pair of parallel guides near the juncture of said first surface and said side wall portions for the guiding of said perimeter edges of said condom package when said condom package is inserted into said container, said second surface and side wall portions thereof forming a concavity facing said first surface approximating the configuration of one side of the condom package where the vertical distance from the top of the concavity to said first surface is about the same as the predetermined thickness of said condom package; and (d) a bottom wall downwardly inclined from said first surface to said second surface, said first surface, second surface, side wall portions and bottom wall collectively defining said receptacle with an open end opposite said bottom wall, said condom package when inserted into said open end along said guides having abutting contact of at least a portion of the surface area of said central portion with said second surface and having abutting contact of said perimeter edges of said condom package with said side wall portions at about the juncture of said side wall portions with said first surface thereby flexing said condom package.

2. The receptacle of claim 1 in which said second surface has a large cut out formed therein.

3. The receptacle of claim 2 in which said first surface has a finger notch therein.

4. The receptacle of claim 3 in which said receptacle is made from plastic.

* * * * *

UNITED STATES PATENT AND TRADEMARK OFFICE
CERTIFICATE OF CORRECTION

PATENT NO. : 5,332,087
DATED : July 26, 1994
INVENTOR(S) : Phillip J. McMahon

It is certified that error appears in the above-indentified patent and that said Letters Patent is hereby corrected as shown below:

In column 4, line 43,

"above" should read --about--.

Signed and Sealed this

Twenty-seventh Day of September, 1994

Attest:

BRUCE LEHMAN

*Attesting Officer*      *Commissioner of Patents and Trademarks*